(12) United States Patent  
Boström

(10) Patent No.: US 11,276,327 B2
(45) Date of Patent: Mar. 15, 2022

(54) ADMINISTRATION MECHANISM FOR A MEDICAMENT DELIVERY TRAINING DEVICE

(71) Applicant: SHL MEDICAL AG, Zug (CH)

(72) Inventor: Anders Boström, Solna (SE)

(73) Assignee: SHL MEDICAL AG, Zug (CH)

( * ) Notice: Subject to any disclaimer, the term of this patent is extended or adjusted under 35 U.S.C. 154(b) by 374 days.

(21) Appl. No.: 16/307,871

(22) PCT Filed: May 10, 2017

(86) PCT No.: PCT/EP2017/061230
§ 371 (c)(1),
(2) Date: Dec. 6, 2018

(87) PCT Pub. No.: WO2017/211531
PCT Pub. Date: Dec. 14, 2017

(65) Prior Publication Data
US 2019/0189029 A1 Jun. 20, 2019

(30) Foreign Application Priority Data
Jun. 8, 2016 (SE) .................... 1650799-8

(51) Int. Cl.
G09B 23/00 (2006.01)
G09B 23/28 (2006.01)
A61M 5/20 (2006.01)

(52) U.S. Cl.
CPC ............ G09B 23/00 (2013.01); G09B 23/285 (2013.01); A61M 5/2033 (2013.01); A61M 2005/2013 (2013.01)

(58) Field of Classification Search
CPC .................................................. G09B 23/285
See application file for complete search history.

(56) References Cited
U.S. PATENT DOCUMENTS 9,132,236 B2  9/2015  Karlsson et al.
9,333,305 B2  5/2016  McLoughlin et al.
(Continued)

FOREIGN PATENT DOCUMENTS

CH        700 473 A1      8/2010
CH        700473 A1  *   8/2010   .......... A61M 5/3155
(Continued)

OTHER PUBLICATIONS

Machine Translation from EPO of Specification for CH700473A1 (Year: 2010).*

(Continued)

Primary Examiner — Malina D. Blaise
Assistant Examiner — Elizabeth Verniers Johnson
(74) Attorney, Agent, or Firm — McDonnell Boehnen Hulbert & Berghoff LLP

(57) ABSTRACT

The present disclosure relates to an administration mechanism (9) for a medicament delivery training device. The administration mechanism (9) comprises a longitudinal medicament delivery member cover (7) configured to be biased in a proximal direction, a rotator (11) configured to be received by the longitudinal medicament delivery member cover (7), the rotator (11) being rotatable relative to the medicament delivery member cover (7), wherein the medicament delivery member cover (7) is linearly displaceable relative to the rotator (11), and wherein the rotator (11) has a guide structure (12) configured to guidedly cooperate with the medicament delivery member cover (7) to cause the rotator (11) to rotate when the medicament delivery member cover (7) is displaced linearly relative to the rotator (11), wherein the medicament delivery member cover (7) is linearly displaceable relative to the rotator (11) from an initial position in which the medicament delivery member cover (7) is prevented from proximal displacement, to a (Continued)

distal position located distally relative to the initial position, thereby rotating the rotator (11) in a first direction, wherein the medicament delivery member cover (7) is linearly displaceable from the distal position to a proximal position located proximally relative to the initial position, thereby rotating the rotator (11) in a second direction opposite to the first direction, and wherein the medicament delivery member cover (7) is linearly displaceable from the proximal position to the initial position.

15 Claims, 7 Drawing Sheets

(56) References Cited

U.S. PATENT DOCUMENTS

| | | | |
|---|---|---|---|
| 9,572,938 B2 | 2/2017 | Julian et al. | |
| 2007/0111175 A1 | 5/2007 | Raven et al. | |
| 2008/0147006 A1* | 6/2008 | Brunnberg | A61M 5/2033 604/136 |
| 2008/0262436 A1* | 10/2008 | Olson | A61M 5/31525 604/198 |
| 2012/0015336 A1* | 1/2012 | Mach | A61M 5/20 434/262 |
| 2013/0172824 A1* | 7/2013 | Smith | A61M 5/31573 604/218 |
| 2014/0276430 A1* | 9/2014 | Baker | A61M 5/1456 604/154 |
| 2015/0032058 A1 | 1/2015 | Karlsson | |
| 2017/0148354 A1* | 5/2017 | Baker | A61M 5/31513 |
| 2017/0357776 A1* | 12/2017 | Baker | G16H 20/17 |

FOREIGN PATENT DOCUMENTS

| | | | |
|---|---|---|---|
| CH | 709126 A2 | 7/2015 | |
| CN | 101868272 A | 10/2010 | |
| CN | 101945681 A | 1/2011 | |
| CN | 103025373 A | 4/2013 | |
| CN | 103068424 A | 4/2013 | |
| DE | 3833138 A1 | 4/1990 | |
| EP | 2633874 A1 | 9/2013 | |
| GB | 426866 A | 4/1935 | |
| TW | I507223 B | 11/2015 | |
| TW | I524908 B | 3/2016 | |
| TW | I527603 B | 4/2016 | |
| WO | 2013032389 A1 | 3/2013 | |
| WO | 2013130973 A1 | 9/2013 | |
| WO | 2014056868 A1 | 4/2014 | |
| WO | 2014164948 A1 | 10/2014 | |
| WO | 2015/075399 A1 | 5/2015 | |
| WO | WO-2016075254 A1 * | 5/2016 | A61M 5/31585 |
| WO | WO-2019058135 A1 * | 3/2019 | G09B 23/285 |

OTHER PUBLICATIONS

Machine Translation from EPO of Specification for CH700473 (Year: 2010).*
English Translation of Abstract of Swedish Patent Application No. 700473 dated Dec. 4, 2018.
English Translation of Abstract of German Patent Application No. 3833138 dated Dec. 4, 2018.
English Translation of Abstract of Swiss Patent Application No. 709126 dated Oct. 18, 2019.
Office Action issued in Swedish Patent Application No. 1650799-8 dated Dec. 7, 2016.
Search Report issued in Taiwanese Patent Application No. 106116480 dated Jun. 14, 2018.

* cited by examiner

ADMINISTRATION MECHANISM FOR A MEDICAMENT DELIVERY TRAINING DEVICE

CROSS REFERENCE TO RELATED APPLICATIONS

The present application is a U.S. National Phase Application pursuant to 35 U.S.C. § 371 of International Application No. PCT/EP2017/061230 filed May 10, 2017 which claims priority to Swedish Patent Application No. 1650799-8 filed Jun. 8, 2016. The entire disclosure contents of these applications are hereby incorporated by reference into the present application.

TECHNICAL FIELD

The present disclosure generally relates to medical devices. In particular, it relates to an administration mechanism for a medicament delivery training device and to a medicament delivery training device for providing medicament delivery training to a user.

BACKGROUND

Medicament delivery devices such as auto-injectors nowadays provide possibilities for the users themselves to handle medicament delivery in an easy, safe and reliable manner.

An auto-injector currently on the market is disclosed in WO2013032389 A1. This document discloses an injection device comprising a housing and a container holder arranged within the housing. The container holder is configured to accommodate a medicament container having a needle attached to one end thereof and a stopper sealingly and slidably arranged inside the medicament container at the other end thereof. The injection device also has a first and a second energy accumulating member arranged in the interior of the housing and adapted to accumulate and store energy, a sleeve that is slidably arranged in relation to the housing, and a plunger holder arranged to be connected to the container holder. The plunger holder is operationally associated with the first energy accumulating member such that due to an output axial force from the first energy accumulating member, the plunger holder and the container holder are axially movable in relation to the housing a predetermined distance towards the proximal end of the injection device from an initial position to a position following needle penetration. The injection device also includes a plunger rod being arranged with a proximal end thereof contactable with the stopper and slidably arranged in relation to the plunger holder and to the container holder. The plunger rod is operationally associated with the second energy accumulating member such that due to an output axial force from the second energy accumulating member the plunger rod is axially movable in relation to the container holder towards the proximal end of the injection device from a locked position to a position following medicament injection, wherein, in the initial position of the plunger holder, movement of the plunger holder towards the proximal end of the injection device is substantially inhibited by at least one first biasable member interacting with the plunger holder, the first biasable member recoiling when being overlapped by an opening and/or recess of the sleeve such that the plunger holder is released. The injection device is in particular suitable for deep penetration applications such as adrenaline injections, as it has an auto-penetration functionality.

Before a user commences a drug administration programme by means of an auto-injector, it may be valuable for the user to undergo training to learn how to administer a drug properly by means of a particular auto-injector. A training device may be used for this purpose.

SUMMARY

In view of the above, a general object of the present disclosure is to provide an administration mechanism for a medicament delivery training device which mimics the behaviour of a known medicament delivery device.

There is hence according to a first aspect of the present disclosure provided an administration mechanism for a medicament delivery training device, wherein the administration mechanism comprises: a longitudinal medicament delivery member cover configured to be biased in a proximal direction, a rotator configured to be received by the longitudinal medicament delivery member cover, the rotator being rotatable relative to the medicament delivery member cover, wherein the medicament delivery member cover is linearly displaceable relative to the rotator, and wherein the rotator has a guide structure configured to guidedly cooperate with the medicament delivery member cover to cause the rotator to rotate when the medicament delivery member cover is displaced linearly relative to the rotator, wherein the medicament delivery member cover is linearly displaceable relative to the rotator from an initial position in which the medicament delivery member cover is prevented from proximal displacement, to a distal position located distally relative to the initial position, thereby rotating the rotator in a first direction, wherein the medicament delivery member cover is linearly displaceable from the distal position to a proximal position located proximally relative to the initial position, thereby rotating the rotator in a second direction opposite to the first direction, and wherein the medicament delivery member cover is linearly displaceable from the proximal position to the initial position.

By means of the three positions of the medicament delivery member cover, obtainable by its mechanical cooperation with the rotator, in particular the guide structure, the general administration procedure of the device disclosed in WO2013032389 A1 may be mimicked, allowing a user to get accustomed to and learn the correct medicament administration procedure. The initial position corresponds to a position in which an injector device of WO2013032389 is ready for use. The distal position corresponds to an administration stage in which the plunger rod is being proximally displaced inside the medicament container, or alternatively to the final position of the plunger. The distal position may to this end correspond to any of the previously mentioned stages of medicament administration, the reason being the very short administration time which is in the order of milliseconds. The proximal position corresponds to a post-administration position of the medicament delivery member cover, which is different from the initial position due to the auto-penetration functionality of the injection device of WO2013032389.

According to one embodiment guide structure has a groove that forms a loop and the medicament delivery member cover has a protrusion configured to run in the groove to allow the medicament delivery member cover to cooperate with the rotator.

According to one embodiment the loop is a closed loop.

According to one embodiment the groove is designed to enable the rotator to rotate back to the same rotational position as when the medicament delivery member cover is in the initial position, when the medicament delivery member cover is displaced from the distal position to the proximal position.

According to one embodiment the loop has a triangular shape.

According to one embodiment a first leg of the triangular-shaped loop is parallel with a central axis of the rotator, wherein a second leg of the triangular shaped loop is at an angle with the first leg, and wherein a third leg of the triangular shaped loop connects the first leg and the second leg.

According to one embodiment a position of the protrusion of the medicament delivery member cover in a region of a first vertex defined by the meeting point of the first leg and the second leg corresponds to the initial position of the medicament delivery member cover.

According to one embodiment a position of the protrusion of the medicament delivery member cover in a region of a second vertex defined by a meeting point of the second leg and the third leg corresponds to the distal position of the medicament delivery member cover.

According to one embodiment a position of the protrusion of the medicament delivery member cover in a region of a third vertex defined by a meeting point of the third leg and the first leg corresponds to the proximal position of the medicament delivery member cover.

According to one embodiment the first leg has a first heel configured to allow the protrusion of the medicament delivery member cover to pass the first heel in the distal direction and to prevent the protrusion from passing the first heel from the initial position in the proximal direction. The medicament delivery member cover is thereby able to maintain its default ready-to-use state, due to it being proximally biased, i.e. biased towards the distal end of the first heel.

According to one embodiment the second leg has a second heel configured to allow the protrusion of the medicament delivery member cover to pass the second heel in a direction from the initial position to the distal position and to prevent the protrusion from entering into the second leg from the distal position in a direction from the distal position to the initial position. An audible click is thus obtained because the protrusion, due to radial flexibility of the medicament delivery member cover, is able to pass above the second heel as the medicament delivery member cover is moved from the initial position to the distal position, and the release of radial tension in the medicament delivery member cover after the protrusion has passed the second heel causes the medicament delivery member cover to obtain its radially unbiased state, resulting in that the protrusion impacts with the groove floor. This provides an indication, similarly to the injection device in WO2013032389 that medicament delivery has commenced/is completed, and that the medicament delivery device may be removed from the injection site.

According to one embodiment the third leg has a third heel configured to allow the protrusion of the medicament delivery member cover to pass the third heel in a direction from the distal position to the proximal position and to prevent the protrusion to pass the third heel from the proximal position in a direction from the proximal position to the distal position.

According to one embodiment the medicament delivery member cover has a radially flexible distal portion, wherein the protrusion is provided on an inner surface of the radially flexible distal portion.

There is according to a second aspect of the present disclosure provided a medicament delivery training device comprising: a housing, and an administration mechanism according to the first aspect, wherein the housing is configured to receive the administration mechanism and wherein the medicament delivery member cover is configured to be rotationally locked relative to the housing.

One embodiment comprises a resilient member configured to bias the medicament delivery member cover in the proximal direction.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which:

FIGS. 2a-2b are perspective views of an administration mechanism of the medicament delivery training device in FIG. 1a;

FIG. 4b is a side view of the rotator in FIG. 4a;

FIG. 8b is a longitudinal section of configuration shown in FIG. 8a.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

The term "proximal end" as used herein, when used in conjunction with an administration mechanism, refers to that end of the administration mechanism which when mounted inside a housing of a medicament delivery training device is closest to the proximal end of the medicament delivery device. The proximal end of the medicament delivery training device is hence that end which is to be pointed towards the site of injection during a simulated medicament expulsion. The same considerations also apply when referring to any component of the administration mechanism. The "distal end" is the opposite end relative to the proximal end. With "proximal direction" and, equivalently, "proximally" is meant a direction from the distal end towards the proximal end, along the central axis of the cap assembly. With "distal direction" or "distally" is meant the opposite direction to "proximal direction".

Figure 1A:
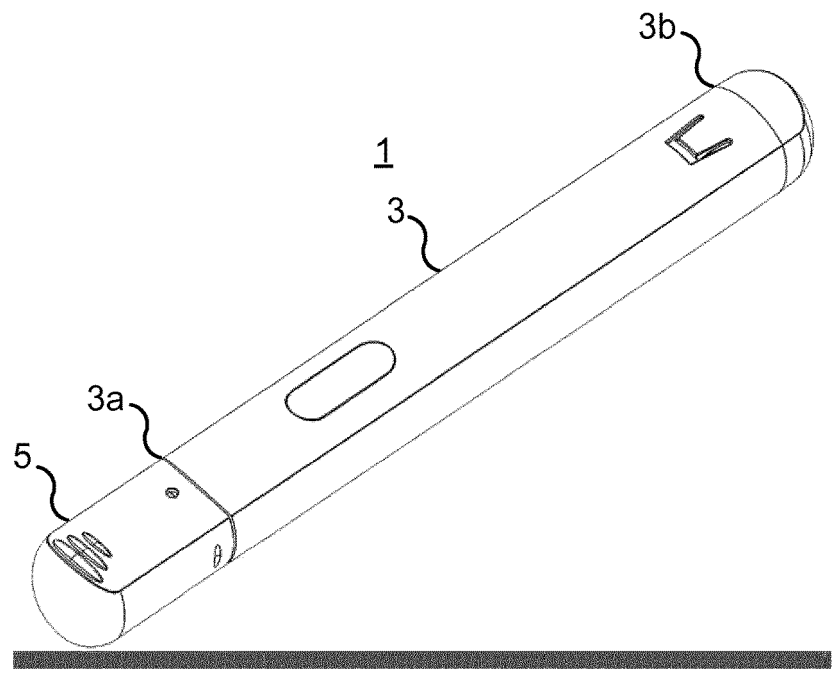
FIG. 1a is a perspective view of an example of a medicament delivery training device.

FIG. 1a shows an example of a medicament delivery training device, in particular a training device for a disposable auto-injector of the type disclosed in WO2013032389. The exemplified medicament delivery training device 1 has a housing 3 having a proximal end 3a and a distal end 3b. The medicament delivery training device 1 furthermore has a removable cap 5 for capping the proximal end 3a of the housing 3, and an administration mechanism arranged inside the housing 3, not shown in FIG. 1a.

Figure 1B:
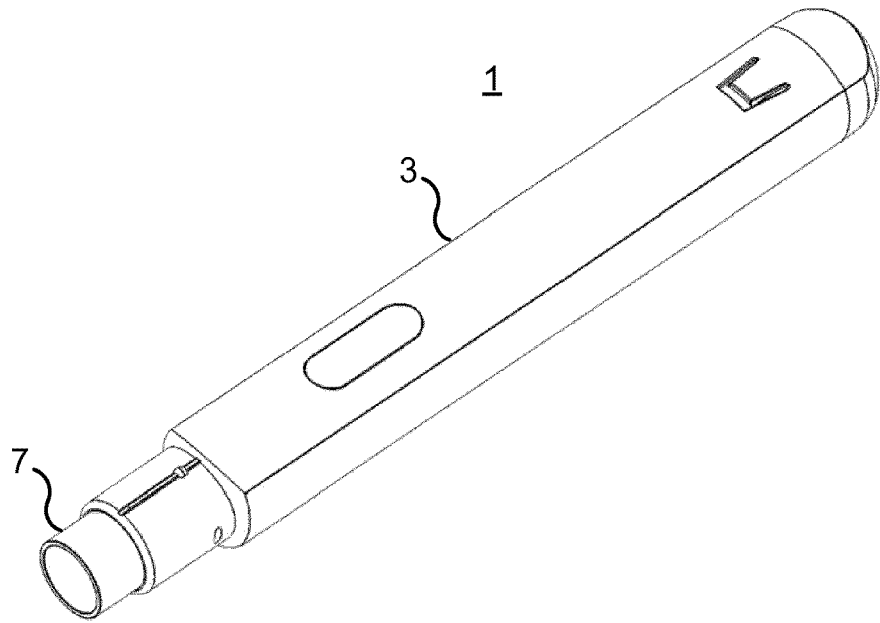
FIG. 1b is a perspective view of the medicament delivery training device in FIG. 1a with the cap removed.

FIG. 1b shows the medicament delivery training device 1 with the cap 5 removed. The medicament delivery training device 1 has a medicament delivery member cover 7 which is linearly displaceable relative to the housing 3 and which in the depicted initial position extends proximally from the proximal end 3a of the housing 3. The medicament delivery member cover 7 forms part of the administration mechanism shown in FIG. 2a, which mimics the administration procedure of a medicament delivery device of the type disclosed in WO2013032389.

Figure 2A:
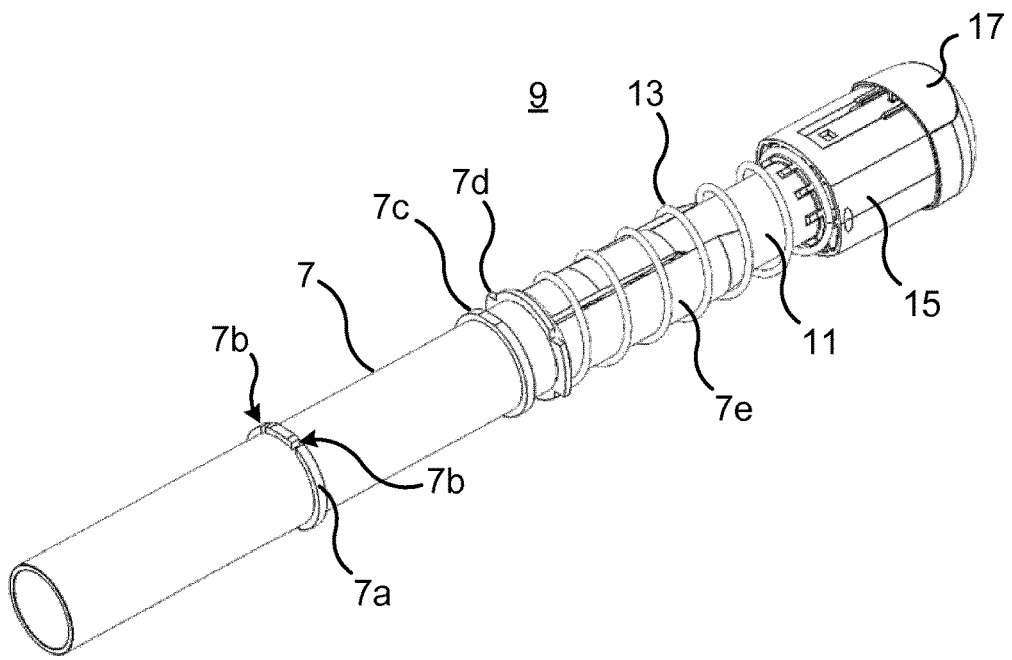

Turning now to FIG. 2a, an example of the administration mechanism is shown. Administration mechanism 9 is configured to be mounted in the housing 3 of the medicament delivery training device 1. The administration mechanism 9 comprises the medicament delivery member cover 7, and a rotator 11. The medicament delivery member cover 7 is configured to provide rotation of the rotator 11 when displaced in either one of the proximal direction and the distal direction.

The medicament delivery member cover 7 is configured to be rotationally locked relative to the housing 3. To this end, the medicament delivery member cover 7 is configured to engage with the housing 3 such that the medicament delivery member cover 7 is linearly displaceable but rotationally locked relative to the housing 3. According to one example, this may be achieved by providing the medicament delivery member cover 7 with an outer flange 7 extending along the circumference of the outer surface of the medicament delivery member cover 7, which outer flange 7a is provided with indentations, cut-outs or recesses 7b configured to engage with corresponding longitudinal axial ribs provided on the inner surface of the housing 3. There may for example be three or more such recesses 7b distributed along the outer flange 7a in the circumferential direction, and the housing 3 may be provided with a corresponding number of longitudinal ribs, each configured to run in a respective recess 7b. The outer surface of the medicament delivery member cover could alternatively be provided with longitudinal axial ribs and the inner surface of the housing could in this case be provided with corresponding recesses in which the longitudinal axial ribs are able to run.

According to the present example, the medicament delivery member cover 7 has a radially outwards extending stop flange 7c which determines the amount that the medicament delivery member cover 7 is able to be displaced in the proximal direction. To this end, the housing 3 may have a radial surface against which the stop flange 7c is configured to bear against when the medicament delivery member cover 7 has been moved a certain distance in the proximal direction. The stop flange 7c is beneficially provided at an axial position on the medicament delivery member cover 7 which enables it to mimic the behaviour of the medicament delivery device disclosed in WO2013032389 post administration, in which the medicament container has been shifted forward in the proximal direction due to its auto-penetration functionality.

The medicament delivery member cover 7 may further optionally comprise another radially outwards extending flange 7d located distally relative to the stop flange 7c, and against which a proximal end of a resilient member 13 is configured to bear against to obtain a proximal biasing of the medicament delivery member cover 7 inside the housing 3. Alternatively, the stop flange 7c could instead have a dual functionality, i.e. to provide a stop for the resilient member 13 instead of the flange 7d, in which case the flange 7d would not be necessary.

The administration mechanism 9 may also comprise the resilient member 13, configured to bias the medicament delivery member cover 7 in the proximal direction. The resilient member 13 may for example be a spring. The resilient member 13 may be configured to receive the rotator 11 and a distal portion 7e of the medicament delivery member cover 7. Proximal displacement of the medicament delivery member cover 7 from its initial position causes the resilient member 13 to become compressed.

The rotator 11 is configured to be received by the distal portion 7e of the medicament delivery member cover 7. The rotator 11 is configured to be rotatable relative to the housing 3. The rotator 11 is hence able to rotate freely relative to the housing 3. The rotator 11 is furthermore configured to be axially locked relative to the housing 3.

Figure 2B:
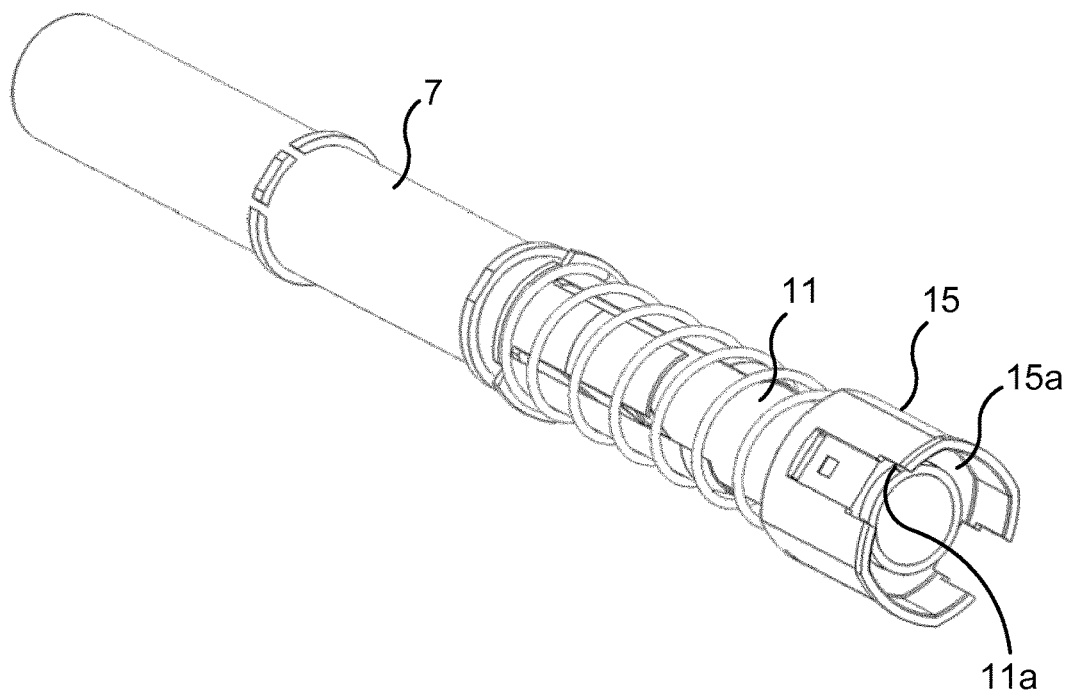

According to the present example, the medicament delivery training device 1 includes an insert member 15 configured to be mounted to the interior of the housing 3. The insert member 15 is configured to be both axially and rotationally locked relative to the housing 3. The rotator 11 is configured to be assembled with the insert member 15, allowing it to freely rotate relative to the insert member 15 but preventing it from axial displacement relative to the insert member 15. FIG. 2b shows the distal end of the administration mechanism 9 with an end cap 17 removed from the insert member 15. The insert member 15 has a through-opening for receiving a distal end portion of the rotator 11. The rotator 11 has a distal stop member 11a configured to bear against a distal radial surface 15a of the insert member 15, at a distal end of the through-opening, and a proximal stop member 11b, e.g. a flange, shown in FIG. 4a, axially displaced relative to each other. The proximal stop member 11b is configured to bear against a proximal radial surface of the insert member 15, at a proximal end of the through-opening. This provides an axial fixation of the rotator 11 relative to the insert member 15, and thus also relative to the housing 3, but allows the rotator 11 to rotate freely relative to the insert member 15.

Figure 3:
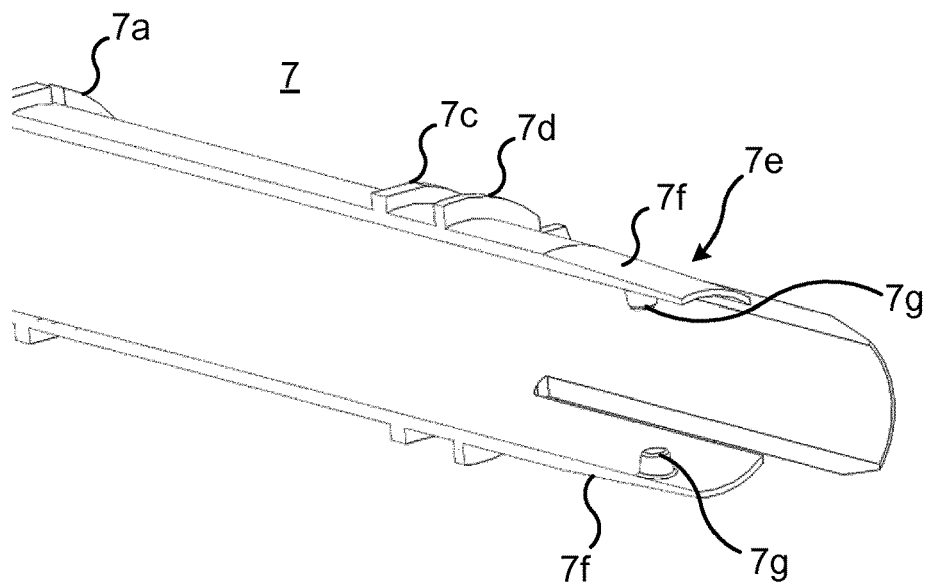
FIG. 3 depicts a perspective view of a longitudinal section of a medicament delivery member cover of the administration mechanism.

FIG. 3 shows a longitudinal asymmetric section of a distal portion of the medicament delivery member cover 7. According to the present example, the medicament delivery member cover 7 has two distal end arms 7f that are flexible in the radial direction. The arms 7f are arranged opposite to each other. Each arm 7f is provided with a respective protrusion 7g, or pin, extending radially inwards.

Figure 4A:
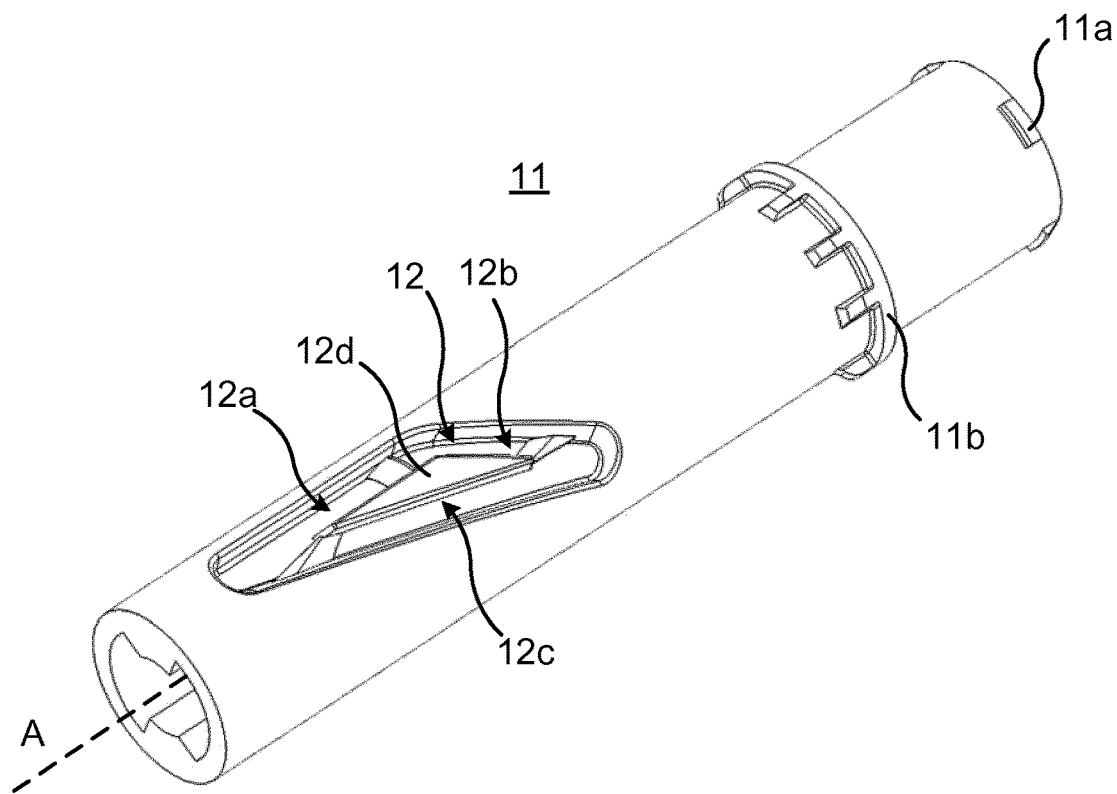
FIG. 4a is a perspective view of a rotator of the administration mechanism.

FIG. 4a shows a perspective view of the rotator 11. The rotator 11 has a guide structure 12 provided on the outer surface of the rotator 11. The exemplified guide structure 12 has a groove which forms a loop. The groove is configured to receive a protrusion 7g, and to allow the protrusion 7g to run in the groove when the medicament delivery member cover 7 is displaced radially. According to the present example, the rotator 11 is provided with two such guide structures 12, one for each protrusion 7g, located essentially 180 degrees apart, although only one can be seen in the figures.

The exemplified loop is triangular-shaped having three legs. A first leg 12a of the triangular-shaped loop is parallel with the longitudinal axis A of the rotator 11. A second leg 12b is angled relative to the first leg 12a, and a third leg 12c connects the first leg 12a and the second leg 12b. The guide structure 12 also has a triangular central elevated portion 12d, with the three legs 12a, 12b and 12c of the triangular-shaped loop being formed around the central elevated portion 12d.

Figure 4B:
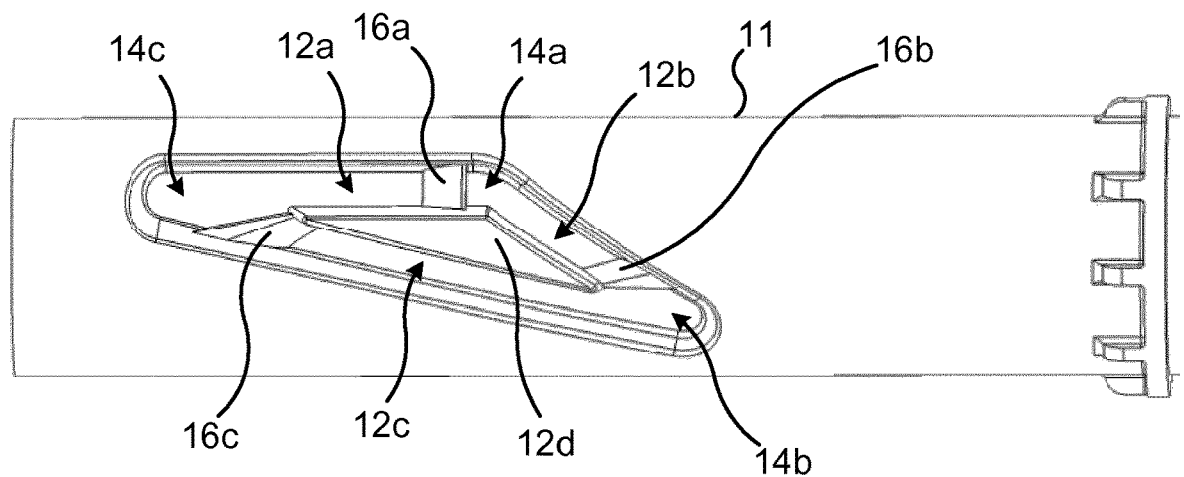

FIG. 4b shows a closer view of the rotator 11 and the guide structure 12. The triangular-shaped loop has three vertices, namely a first vertex 14a which forms the connection between the first leg 12a and the second leg 12b, a second vertex 14b which forms the connection between the second leg 12b and the third leg 12c, and a third vertex 14c which forms the connection between the third leg 12c and the first leg 12a. Moreover, according to the exemplified rotator 11, the guide structure 12 has a first heel 16a located along the first leg 12a in a region of the first vertex 14a. The first heel 16a is configured to allow a protrusion 7g of the medicament delivery member cover 7 running in the groove forming the triangular-shaped loop to pass in a distal direction, i.e. in a direction from the third vertex 14c to the first vertex 14a, and to prevent the protrusion to pass it in the proximal direction.

The guide structure 12 also has a second heel 10, located along the second leg 12b in a region of the second vertex 14b. The second heel 16b is configured to allow a protrusion 7g of the medicament delivery member cover 7 running in the groove forming the triangular-shaped loop to pass in a direction from the first vertex 14a towards the second vertex 14b, and to prevent the protrusion 7g to pass it in the opposite direction, i.e. the direction from second vertex 14b towards the first vertex 14a.

The guide structure 12 also has a third heel 16c, located along the third leg 12c in a region of the third vertex 14c. The third heel 16c is configured to allow a protrusion 7g running in the groove forming the triangular-shaped loop to pass in a direction from the second vertex 14b towards the third vertex 14c, and to prevent the protrusion 7g to pass it in the opposite direction, i.e. the direction from the third vertex 14c towards the second vertex 14b.

Each of the heels 16a, 16b and 16b may be wedge-shaped or essentially wedge-shaped, having a ramp structure at one end, corresponding to the above-defined passing directions, and an essentially radial surface at the other end.

Due to the above-described configuration with the heels 16a-16c, the loop defines a unidirectional loop or circuit for a protrusion 7g, as will be explained in more detail in the following where the function of the administration mechanism 9 will be described with reference to FIG. 1a and FIGS. 5-8b.

Figure 5:
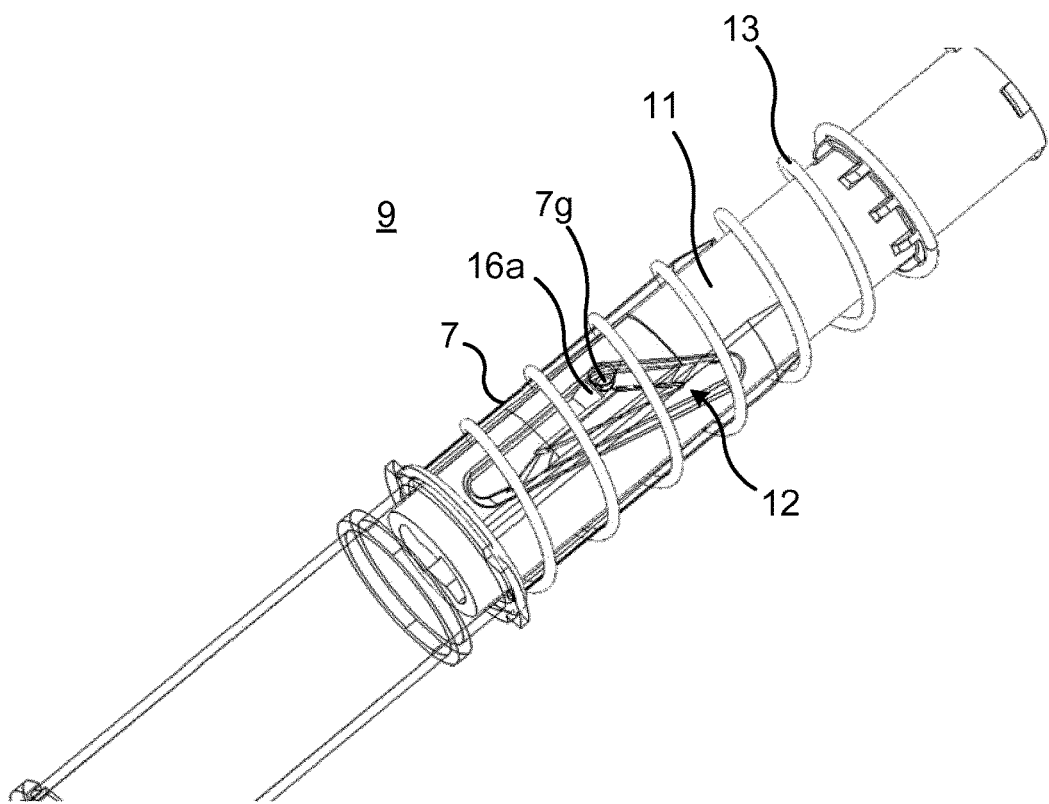
FIG. 5 is a perspective view of the administration mechanism in FIG. 2a with the medicament delivery member cover having been made transparent in the initial position to illustrate the cooperation between the medicament delivery member cover and the rotator.

FIG. 1b shows the medicament delivery training device 1 in a state which corresponds to a ready-to-use state of the medicament delivery device disclosed in WO2013032389. In this state, the medicament delivery member cover 7 is in an initial position, extending from the housing 3. FIG. 5 shows a portion of the administration mechanism 9, with the medicament delivery member cover 7 having been made transparent for the purpose of illustrating the cooperation between the medicament delivery member cover 7 and the rotator 11. In this state, the medicament delivery member cover 7 is in an initial position relative to both the housing 3 and the rotator 11. The protrusion 7g is arranged in the guide structure 12, in a region of the first vertex 14a, distally from the first heel 16a. Due to the proximal biasing provided by the resilient member 13, the protrusion 7g rests against a radial distal end face of the first heel 16a.

Figure 6A:
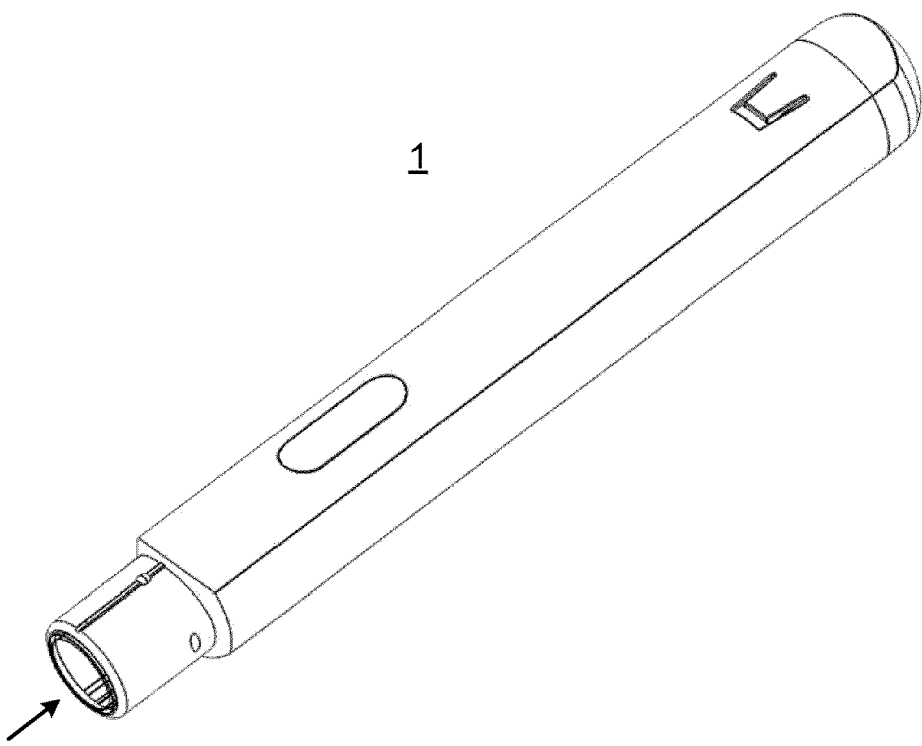
FIG. 6a depicts a perspective view of the medicament delivery training device during activation thereof.
Figure 6B:
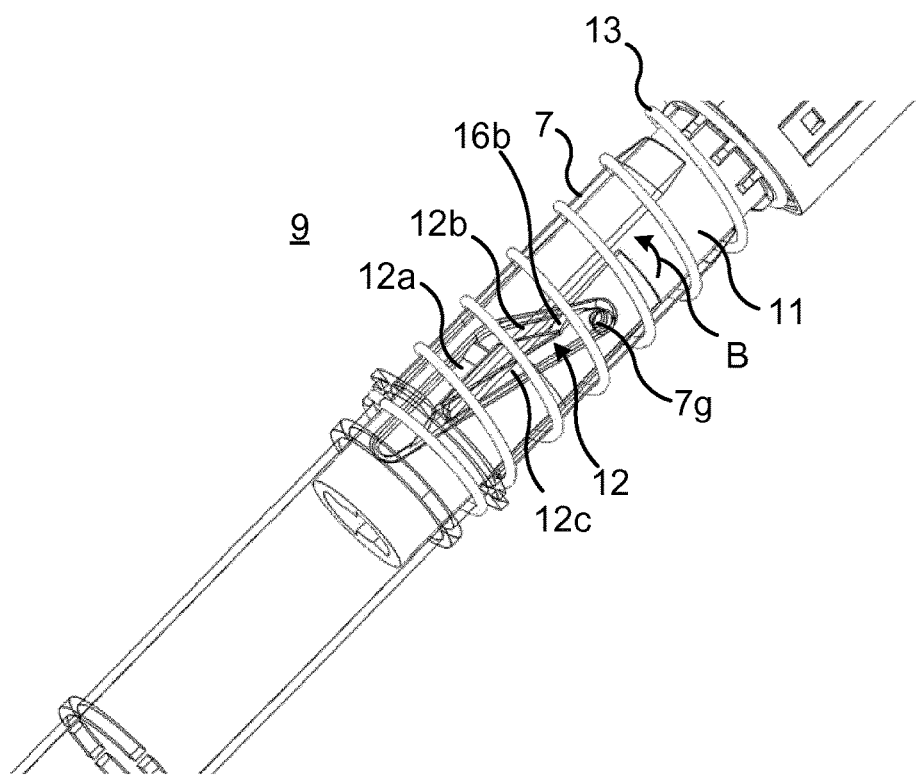
FIG. 6b is a perspective view of the administration mechanism in FIG. 2a with the medicament delivery member cover being transparent in the distal position thereof.

FIG. 6a shows the medicament delivery training device 1 in an activated state, in which the medicament delivery member cover 7 has been displaced in the distal direction and essentially fully received by the housing 3. FIG. 6b shows the administration mechanism 9 when the medicament delivery training device 1 is in the activated state. In the activated state, the medicament delivery member cover 7 has been pushed into the housing 3, resulting in that the protrusion 7g has been moved from the initial position to a distal position which is arranged distally relative to the initial position. The protrusion 7g is hence moved along the second leg 12b which is at an angle relative to the first leg 12a. Since the medicament delivery member cover 7 is rotationally locked relative to the housing 3 and the rotator 11 is allowed to rotate relative to the housing 3, the rotator 11 is rotated in a first direction as shown by arrow B. The protrusion 7g is furthermore allowed to move over or pass the second heel 16b, as the arm provided with the protrusion 7g is flexed radially outwards, resulting in an audible "click" after having passed the second heel 16b. This corresponds to a click provided by the injector disclosed in WO2013032389, allowing the user to learn the behaviour of that injector. The protrusion 7g is not allowed to return to the second leg 12b from the distal position due to the second heel 16b. The protrusion 7g can thus now only travel proximally along the third leg 12c when the medicament delivery member cover 7 is released from its retracted position relative to the housing 3, i.e. from the distal position.

Figure 7A:
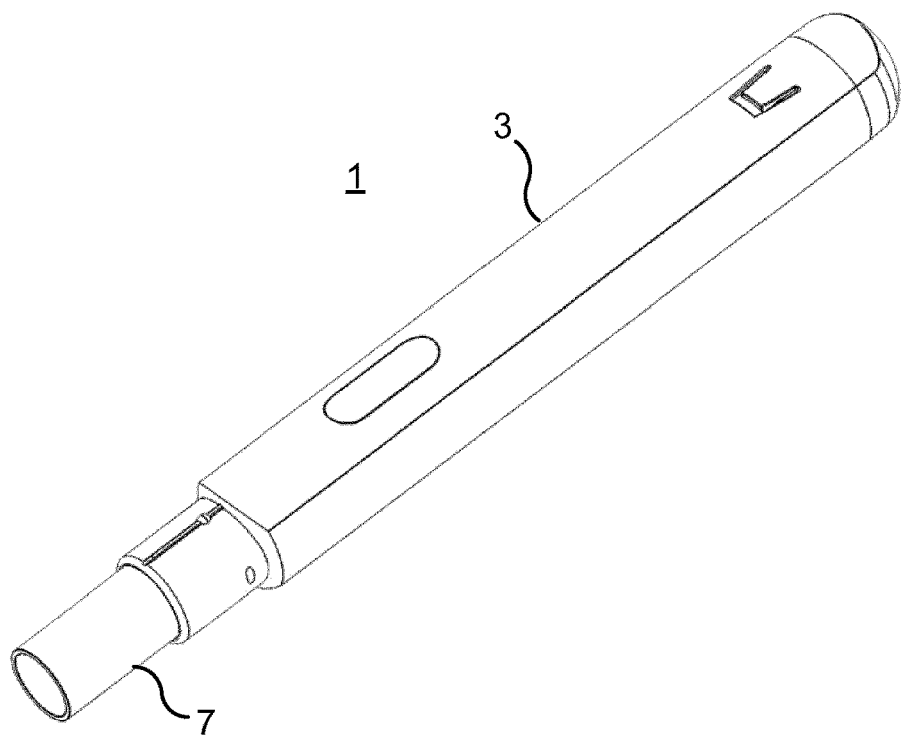
FIG. 7a is a perspective view of the medicament delivery training device after use.

FIG. 7a shows the medicament delivery training device 1 in a state when administration has been completed and the medicament delivery member cover 7 has been released from its proximally biased distal position shown in FIGS. 6a and 6b. It should here be noted that in this state the medicament delivery member cover 7 extends further from the housing 3 than in the initial position shown in FIG. 1b. This mimics the auto-penetration functionality of the injector disclosed in WO2013032389, in which the medicament container and the needle have been shifted forward but are still covered by the medicament delivery member cover.

Figure 7B:
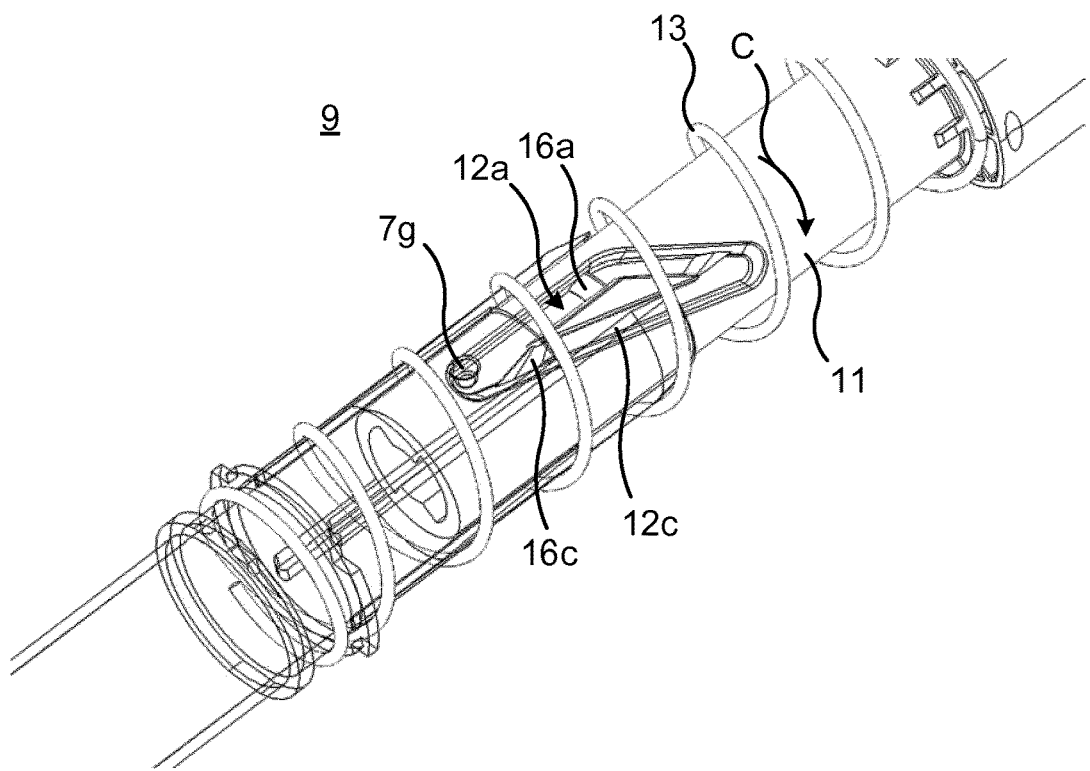
FIG. 7b is a perspective view of the administration mechanism in FIG. 2a with the medicament delivery member cover being transparent in the proximal position thereof.

FIG. 7b shows the administration mechanism 9 when the medicament delivery training device 1 is in a final state, after the completion of medicament administration, or to be more precise, the simulation or mimicking of medicament administration. As the medicament delivery member cover 7 is released, it moves along the third leg 12c, and passes the third heel 16c, obtaining the proximal position shown in FIG. 7b. The proximal position is located proximally relative to the initial position. Due to the angled orientation of the third leg 12c relative to the axially parallel first leg 12a, the rotator 11 is rotated in a second direction, opposite to the first direction, to its initial rotational position, as illustrated by arrow C.

Figure 8A:
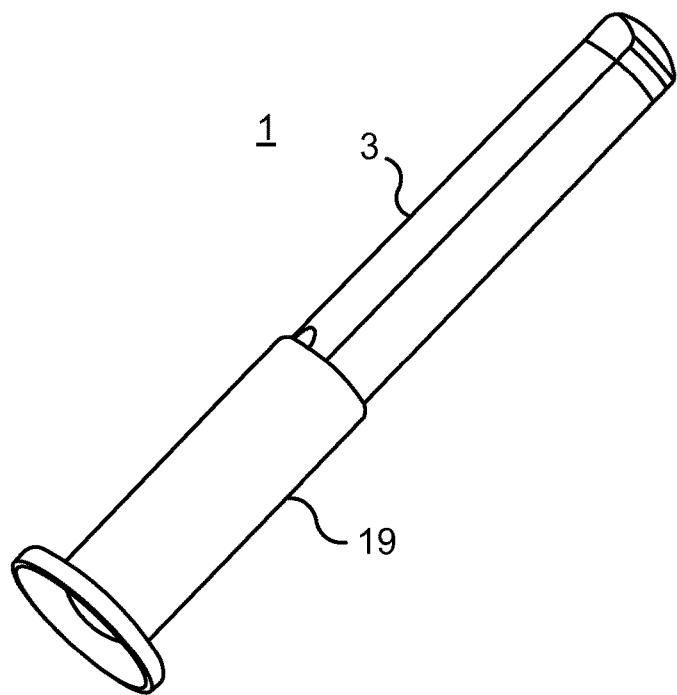
FIG. 8a shows a perspective view of the medicament delivery training device to together with a re-loader.
Figure 8B:
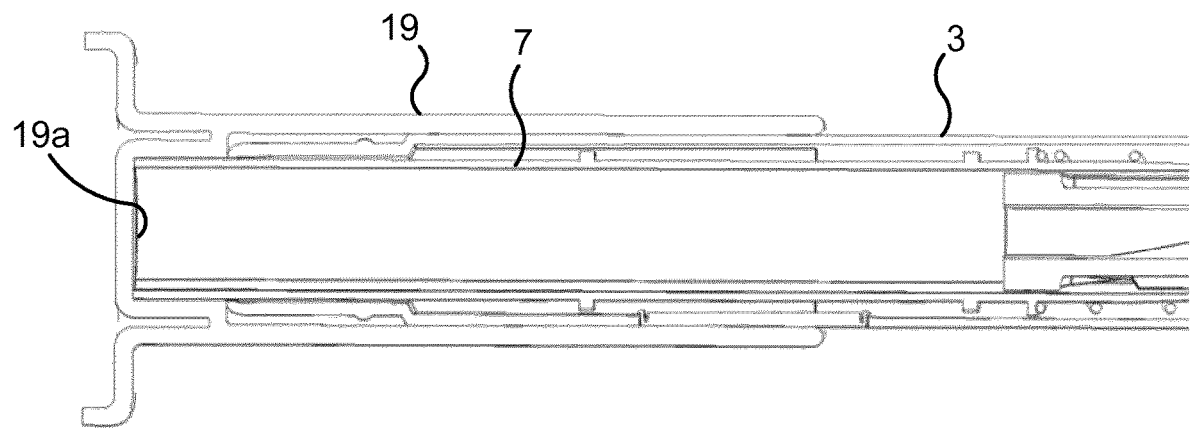

A user may at this stage re-load the medicament delivery training device 1, for example by means of a specifically designed re-loader 19, shown in FIG. 8a. The medicament delivery training device 1 may be placed on the re-loader, which may be standing on a horizontal surface, with the proximal end of the medicament delivery training device 1 facing the re-loader 19. As the medicament delivery training device 1 pushed into an opening of the re-loader and reaches a bottom surface 19a of the re-loader 19, the medicament delivery member cover 7 will be pushed distally into the housing 3. Due to the third heel 16c, displacement of the medicament delivery member cover 7 in the distal direction results in that the protrusion 7g is moved along the first leg 12a, allowing it to pass the first heel 16a as the arm that is provided with the protrusion 7g is flexed radially outwards. The medicament delivery training device 1 is thereby set in the ready-to-use state shown in FIGS. 1b and 5, enabling the user to repeat the medicament administration training procedure.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. An administration mechanism for a medicament delivery training device that has no medicament container, no medicament, no medicament container holder, no needle, no plunger rod, and no plunger holder, wherein the administration mechanism comprises:
    a longitudinal medicament delivery member cover slidably positioned within a housing of the training device, the medicament delivery member cover comprising,
    an outer surface having a terminal distal end;
    a flange extending radially outward from the outer surface at a location that is proximal to the distal end; and
    a distal end arm formed from a cut-out in the outer surface, where the cut-out begins proximally of the location of the flange and ends at the terminal distal end, where the distal end arm is flexible in an outward radial direction and comprises a protrusion projecting radially inward;
    a resilient member surrounding an outer distal portion of the outer surface, where the resilient member comprises a distal end and a proximal end that engages the outer surface at a location proximal to the cut-out such that the medicament delivery member cover is biased axially in a proximal direction;
    a rotator positioned within the distal portion of the medicament delivery member cover, the rotator being rotatable relative to the medicament delivery member cover; and
    an insert positioned within the housing, where the insert is axially fixed relative to the rotator while allowing the rotator to freely rotate relative to the insert,
    wherein the insert further comprises a stop surface that abuts the distal end of the resilient member,
    wherein the medicament delivery member cover is linearly displaceable relative to the rotator, and wherein the rotator has a guide structure that is slidably engaged with the protrusion such that the rotator will rotate when the medicament delivery member cover is displaced linearly relative to the rotator,
    wherein the medicament delivery member cover is linearly displaceable relative to the rotator from an initial position in which the medicament delivery member cover is prevented from proximal displacement, to a distal position located distally relative to the initial position, thereby rotating the rotator in a first direction, where movement to the distal position causes the distal end arm to flex radially outward and then to flex radially inward causing an audible click when the medicament delivery member cover has reached the distal position,
    wherein the medicament delivery member cover is linearly displaceable from the distal position to a proximal position located proximally relative to the initial position, thereby rotating the rotator in a second direction opposite to the first direction,
    wherein the linear displacement of the medicament delivery cover when moving from the distal position to the proximal position is equal to an axial distance between the location of the flange and an inner surface of the housing when the medicament delivery cover is in the distal position, and
    wherein the medicament delivery member cover is linearly displaceable from the proximal position to the initial position.

2. The administration mechanism as claimed in claim 1, wherein the guide structure has a groove that forms a loop and the medicament delivery member cover has a protrusion configured to run in the groove to allow the medicament delivery member cover to cooperate with the rotator.

3. The administration mechanism as claimed in claim 2, wherein the loop is a closed loop.

4. The administration mechanism as claimed in claim 2, wherein the groove is designed to enable the rotator to rotate back to the same rotational position as when the medicament delivery member cover is in the initial position, when the medicament delivery member cover is displaced from the distal position to the proximal position.

5. The administration mechanism as claimed in claim 3, wherein the loop has a triangular shape.

6. The administration mechanism as claimed in claim 5, wherein a first leg of the triangular-shaped loop is parallel with a central axis of the rotator, wherein a second leg of the triangular shaped loop is at an angle with the first leg, and wherein a third leg of the triangular shaped loop connects the first leg and the second leg.

7. The administration mechanism as claimed in claim 6, wherein a position of the protrusion of the medicament delivery member cover in a region of a first vertex defined by the meeting point of the first leg and the second leg corresponds to the initial position of the medicament delivery member cover.

8. The administration mechanism as claimed in claim 6, wherein a position of the protrusion of the medicament delivery member cover in a region of a second vertex defined by a meeting point of the second leg and the third leg corresponds to the distal position of the medicament delivery member cover.

9. The administration mechanism as claimed in claim 6, wherein a position of the protrusion of the medicament delivery member cover in a region of a third vertex defined by a meeting point of the third leg and the first leg corresponds to the proximal position of the medicament delivery member cover.

10. The administration mechanism as claimed in claim 6, wherein the first leg has a first heel configured to allow the protrusion of the medicament delivery member cover to pass the first heel in the distal direction and to prevent the protrusion from passing the first heel from the initial position in the proximal direction.

11. The administration mechanism as claimed in claim 6, wherein the second leg has a second heel configured to allow the protrusion of the medicament delivery member cover to pass the second heel in a direction from the initial position to the distal position and to prevent the protrusion from entering into the second leg from the distal position in a direction from the distal position to the initial position.

12. The administration mechanism as claimed in claim 6, wherein the third leg has a third heel configured to allow the protrusion of the medicament delivery member cover to pass the third heel in a direction from the distal position to the proximal position and to prevent the protrusion to pass the third heel from the proximal position in a direction form the proximal position to the distal position.

13. The administration mechanism as claimed in claim 2, wherein the medicament delivery member cover has radially flexible distal portion, wherein the protrusion is provided on an inner surface of the radially flexible distal portion.

14. A medicament delivery training device comprising:
   a housing, and
   an administration mechanism as claimed in claim 1,
   wherein the housing is configured to receive the administration mechanism and wherein the medicament delivery member cover is configured to be rotationally locked relative to the housing.

15. The medicament delivery training device as claimed in claim 14, comprising a resilient member configured to bias the medicament delivery member cover in the proximal direction.

* * * * *